United States Patent [19]

Rouge et al.

[11] B 4,000,424
[45] Dec. 28, 1976

[54] DRIVE MECHANISM FOR AN X-RAY ANTI-SCATTER GRID

[75] Inventors: Serge Rouge, Montrouge; Richard Dumesnil, Carrieres sur Seine, both of France

[73] Assignee: U.S. Philips Corporation, New York, N.Y.

[22] Filed: May 5, 1975

[21] Appl. No.: 574,616

[44] Published under the second Trial Voluntary Protest Program on March 2, 1976 as document No. B 574,616.

[30] Foreign Application Priority Data

May 8, 1974  France ............................ 74.15879

[52] U.S. Cl. .......................... 250/445 T; 250/452; 250/509
[51] Int. Cl.² ....................................... H01J 35/16
[58] Field of Search ............... 250/452, 445 T, 508, 250/509, 445

[56] References Cited

UNITED STATES PATENTS

| | | | |
|---|---|---|---|
| 2,720,596 | 10/1955 | Acker | 250/445 T |
| 3,684,885 | 8/1972 | Cook | 250/509 |
| 3,770,955 | 11/1973 | Tomita | 250/445 T |

*Primary Examiner*—Craig E. Church
*Attorney, Agent, or Firm*—Frank R. Trifari

[57] ABSTRACT

A drive mechanism for the anti-scatter grid of an X-ray apparatus, notably a tomography apparatus.

For focussing the grid with respect to the X-ray source, use is made of a pin which engages a diametrical groove provided in a drive disc. The disc is coupled to the rotatably arranged grid. So as to avoid overloading of the pin, the groove is provided with a run-out, while the pin is connected to the disc by way of a resetting member which also serves as an alternative drive for the disc.

2 Claims, 5 Drawing Figures

DRIVE MECHANISM FOR AN X-RAY ANTI-SCATTER GRID

The invention relates to a drive mechanism for the anti-scatter grid of an X-ray apparatus, comprising a driven parallelogram-like supporting arm construction which is pivotable in all directions about a pivot, an X-ray source being connected on one side of the pivot, on the other side of the pivot there being provided an image section comprising the said anti-scatter grid and a drive disc which is coupled to the anti-scatter grid and which is provided with a diametrically extending groove which cooperates with a drive pin, the said drive pin being connected to the supporting arm construction on the side of the pivot which is remote from the X-ray source and being slidable under spring pressure with respect to the supporting arm construction in a direction perpendicular to the plane of the disc.

In known X-ray apparatus comprising drive mechanisms for the anti-scatter grid of the kind set forth, use is made of the difference in distance, inherent of the construction, from the pivot of the supporting arm construction which exists between the location where the image section is connected to the supporting arm construction and the location where the drive of the anti-scatter grid is connected to the supporting arm construction for making the anti-scatter grid rotate in synchronism with the X-ray source. The said difference in distance gives rise to trajects of points on the supporting arm construction which are situated at a different distance from the pivot, the said trajects having a similar shape but a different size. The difference in size is utilized to make the said pin drive the disc by way of a diametrical groove.

The known drive mechanism has a number of drawbacks which are due to the fact that the driven point of the supporting arm construction is also subject to movement trajects having a substantially varying radius of curvature or a comparatively small radius of curvature. Because the drive torque for the disc is determined by the product of the available drive force — often varying in time — and the distance between the end of the drive pin which cooperates with the disc and the centre of the disc, it often occurs that — if the said distance becomes too small — either the required drive torque can no longer be delivered or the loading of the drive pin becomes too high. In the known X-ray apparatus it was attempted to avoid overloading by interrupting the engagement of the drive pin in the disc by hand. To this end, the drive pin was arranged to be slidable against spring pressure with respect to the supporting arm construction. Because in the case of exposure techniques involving small movement curves — such as the comparatively small circular traject used for tomography — a non-driven anti-scatter grid does not cause undesired shadow effects of the radiation-absorbing laminations of the grid on the X-ray film, use has also be made already of a disc provided with a groove having a central widened portion which has dimensions which are larger than the traject to be described by the drive pin. In this special case the drive pin does not drive the disc.

The invention has for its object to provide a drive mechanism for an anti-scatter grid in which overloading can be avoided by the automatic uncoupling of the drive pin and the drive disc, after which the coupling is also automatically restored, whilst during the uncoupling an alternative, overload-preventing drive of the disc is ensured.

To this end, the device according to the invention is characterized in that the diametrical groove comprises an inclined portion which serves as a run-out for the drive pin and which has a maximum height which is substantially equal to the maximum depth of the diametrical groove, the drive pin being arranged in a resetting member which cooperates with the disc under friction and which bears on the one side against the disc under spring pressure and which on the other side is slidable in the lateral direction with respect to the disc under the force of two reset springs which are connected on the one end to the disc, and on the other end to the resetting member.

The invention will be described in detail hereinafter with reference to the drawing.

FIG. 1 diagrammatically shows a tomography apparatus in which use is made of a drive mechanism according to the invention.

Figure 1:
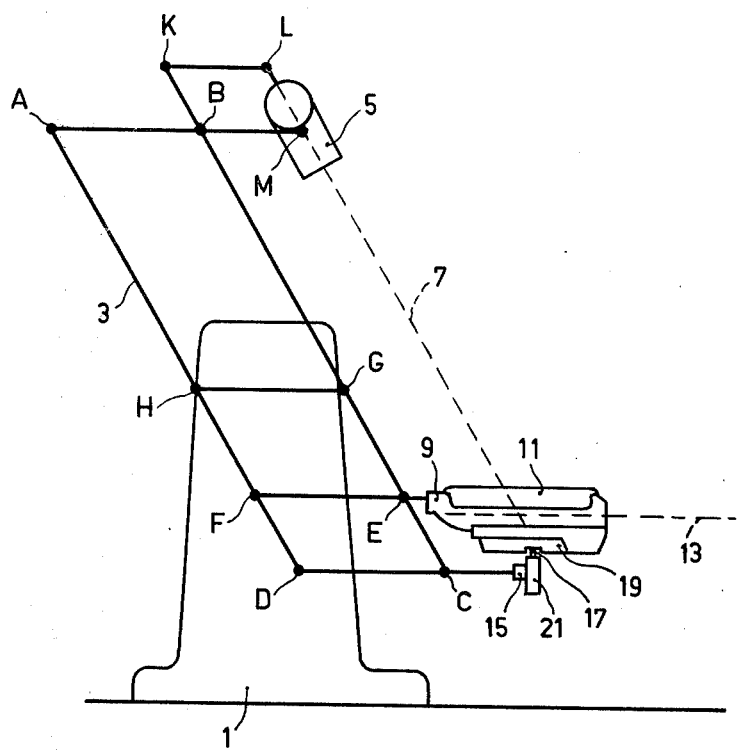

The known tomography X-ray apparatus shown in FIG. 1 comprises a frame 1 in which a supporting arm construction 3 is suspended, the said construction being composed of a main parallelogram ABCD and two sub-parallelograms ABEF and ABGH. The main parallelogram ABCD is suspended to be pivotable in all directions in the frame 1 at the points G and H. The parallelogram ABCD can pivot about the axis HG as well as about axes perpendicular to the plane of the drawing through the points H and G by means of a known drive acting on the parallelogram ABCD. Therefore, the frame points H and G are actually ball joints. The supporting arm construction 3 furthermore comprises a parallelogram BKLM which serves for the suspension of an X-ray source 5. The central beam 7 of the X-ray source 5 is kept parallel to the arm BC of the supporting arm construction 3 in all circumstances by the parallelogram BKLM, and is always situated in the plane of the parallelogram ABCD. The extension of the arm FE has connected thereto a support 9 for an anti-scatter grid 11 and an X-ray film cassette 13 which is denoted by broken lines. The anti-scatter grid 11 and the X-ray film cassette 13 are of a commonly used, known kind. The anti-scatter grid 11 is arranged to be rotatable in the support 9. In conjunction with the film cassette 13 and the support 9, the grid 11 constitutes the so-termed image section of the X-ray apparatus. In the prolongation of the arm DC there is situated a supporting arm 15 (see also FIG. 2) for a drive pin 17 which cooperates with a drive disc 19 — provided in the support 9 and rotatable therein — which is coupled in known manner (not shown) to the anti-scatter grid 11. The central beam 7 is always directed towards the centre of the X-ray film cassette 13.

The patient table (not shown for the sake of clarity) is situated between the X-ray source 5 and the anti-scatter grid 11. The patient table may be arranged to be immobile, but may alternatively be coupled to a drive in the frame 1 for turning the parallelogram ABCD and axis GH.

It is to be noted that in an X-ray apparatus as shown in FIG. 1 — used in particular for tomography — the support 9 is always displaced parallel to itself. To this end, the arms FE and DC are coupled to a parallelogram construction which transfers rotations of the parallelogram ABCD about the axis HG to the arms FE and DC which are rotatable about their own axis. The plane of the said known parallelogram construction — not shown for the sake of clarity — is always transverse to the plane of the parallelogram ABCD.

Figure 2:
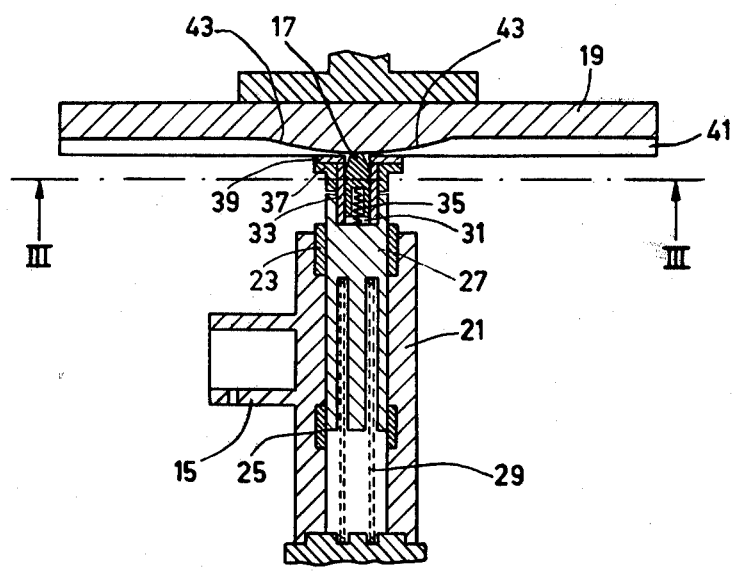
FIG. 2 is a sectional view of a drive mechanism according to the invention.

The preferred embodiment of a drive mechanism according to the invention which is shown in FIG. 2 comprises — as already stated with reference to FIG. 1 — a supporting arm 15 which is provided on the prolongation of the parallelogram arm DC. On the supporting arm 15 there is provided a bearing sleeve 21, the central axis of which is perpendicular to the plane of the drive disc 19. In the bearing sleeve 21 there are provided two self-lubrication bearings 23 and 25 for guiding a piston 27 which is slidable in the sleeve 21 under the force of a spring 29. The piston 27 is provided on its upper side with a bore 31 for a bearing sleeve 33 which serves to guide the drive pin 17. The pin 17 is slidable in the downward direction (in the drawing) against the force of a spring 35 provided in the bearing sleeve 33. The length of the bearing sleeve 33 is chosen to be such that the part thereof which projects above the bore 31 is used for journalling a collar 37 in the transverse direction, the said collar 37 being rotatable about the sleeve 33 and being provided with a friction layer 39. The collar 37 and the friction layer 39 are provided with concentrical openings wherethrough the drive pin 17 is inserted.

The circular drive disc 19 is provided with a diametrically extending groove 41 having a rectangular cross-section. During cooperation with the disc 19, the pin 17 bears under spring pressure against the bottom of the groove 41. The groove 41 comprises an inclined portion 43 which is symmetrically arranged with respect to the centre of the disc, its maximum height being substantially or completely equal to the maximum depth of the groove. The position of the pin 17 with respect to the disc 19 shown in FIG. 2 is the position in which the engagement between the two components has just been terminated. The pin 17 is always pressed against the bottom of the groove 41 due to the bias of the spring 35. The friction layer 39 is always pressed against the surface of the disc 19, biased by the spring 29. The smallest outer dimensions of the rectangular friction layer 39 and the rectangular collar 37 are, of course, larger than the width of the groove 41. Any material having a sufficiently high friction coefficient can in principle be used for the friction layer. The collar 37 and the friction layer 39 can also be made as one integral unit. One end of springs 45 and 49 is connected to the disc 19 at diametrically opposed points, the other end of the said springs being connected to the collar 37. The connecting line between the connection points of the springs 43 and 45, situated near the circumference of the disc, is perpendicular to the longitudinal direction of the groove 41. In any position of the pin 17 with respect to the disc the springs are biased. The width of the groove 41 is chosen to be slightly larger than the diameter of the pin 17. The friction layer 39 and the collar 37 together constitute the resetting member.

Figure 3:
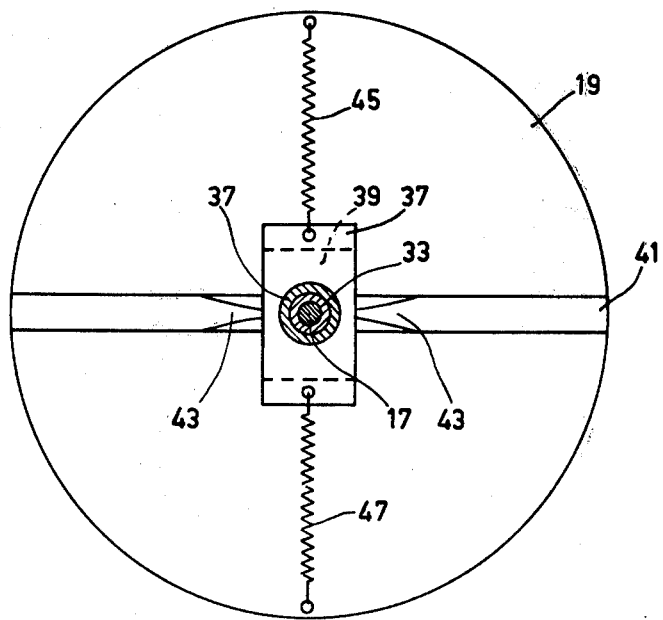
FIG. 3 is a bottom sectional view taken along the line III—III in FIG. 2.

The operation of the drive mechanism already described with reference to the FIGS. 1, 2 and 3 will be described in detail hereinafter with reference to the FIGS. 4 and 5.

For a proper understanding of the invention, the description will be based on a traject of X-ray source and image section which is commonly used for tomography in practice, i.e. a hypocycloid. When a spatial hypocycloid traject is imposed on the supporting arm construction, the traject of the drive pin 17 will also have mainly a spatial hypocycloid shape, even though the size of this traject deviates from the traject imposed on the supporting arm construction. The projection of the disc 19 of such a spatial hypocycloid traject is denoted by the uninterrupted curve HYP shown in FIG. 4.

Figure 4:
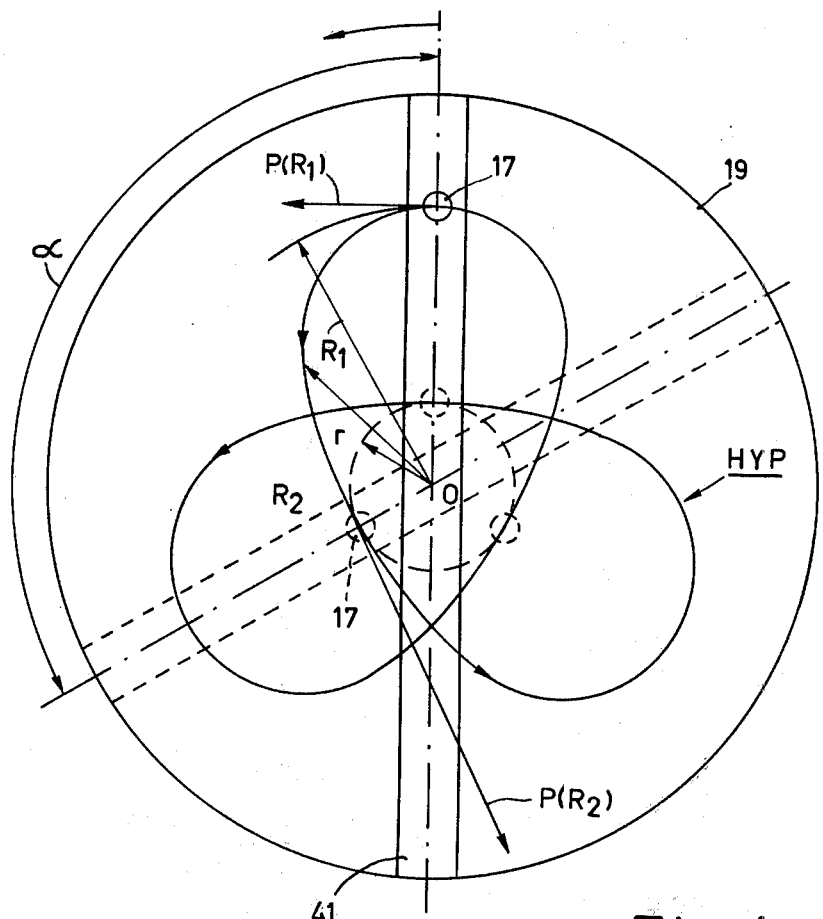
FIG. 4 is a bottom view of the drive disc in which one of the trajects to be described by the drive pin is diagrammatically shown to be projected on the surface of the disc.
Figure 5:
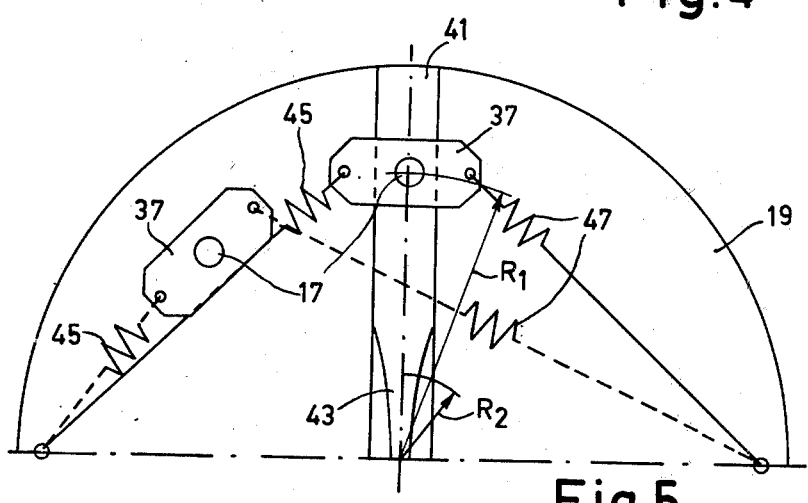
FIG. 5 is a bottom view of the reset member used in the drive mechanism shown in the FIGS. 1, 2 and 3.

It is assumed that at the start the drive pin 17 is situated in the position of the hypocycloid traject shown in FIG. 4, at a distance R from the centre O of the disc 19 in the groove 41. It is also assumed that the torque $P \times r$, exerted by the pin 17 on the disc 19 during the completion of the hypocycloid traject, is substantially constant. The drive torque exerted by the pin 17 on the disc 19 in the starting position amounts to $P(R_1) \times R_1$. As the pin 17 completes its traject in the direction of the arrow in FIG. 4, the radius $r$ continuously decreases to a minimum value $R_2$ in the position in which the disc 19 has been rotated counter-clockwise through an angle $\alpha$. In the position $r = R_2$, the drive torque exerted on the disc 19, therefore, amounts to $P(R_2) \times R_2$, $P(R_2)$ being substantially larger than $P(R_1)$. Because in practice a drive is usually chosen to be so heavy that the starting torque $(P(R_1) \times R_1)$ can be amply produced, the decrease in radius, amounting to $R_2 - R_1$, in this case indeed gives rise to an unacceptably high load $P(R_2)$ of the drive pin. Thanks to the inclination 43 in the groove 41, the pin 17 can and must run out of the groove 41, so that the admissible load of the pin is not exceeded. During running out, the spring 35 is compressed. After the pin has run out of the groove, the driving of the disc 19 is taken over by the friction layer 39 on the collar 37 (see FIGS. 2 and 5). The tension in the spring 29, being substantially larger than the tension in the spring 35, ensures continuity in the driving of the disc. After the pin has run out of the groove, slippage occurs between the friction layer 39 and the surface of the disc 19, so that any shocks are absorbed. As is illustrated in the FIG. 5, a resetting force is exerted on the collar 37 by the springs 45 and 47, with the result that the pin is returned to the groove 41. In theory, the pin can of course return in the groove at a radius from O such that overloading of the pin could occur again. However, in that case the inclination 43 would cause anewed running out of the pin. In the present case the parameters involved — for example, the spring constant of the springs 29, 45 and 47 and the friction coefficient of the friction layer 39 — are chosen to be such, however, that for the given traject of the drive pin after the run-out, a timely return in the groove 41 at an adequate distance from O is ensured. For the illustrated hypocycloid, the run-out is repeated twice more.

Even though the drive according to the invention was illustrated with reference to a hypocycloid traject described by the pin 17, it will be obvious that the drive is generally useful for trajects where a substantial variation occurs in the radius of curvature or where the radius of curvature is comparatively small. Examples of such trajects are the ellipses which commonly occur in tomography, and the small circle often used in zonography.

It is also to be noted that when the parallelogram ABCD rotates (see FIG. 1) about the axes through H and G, perpendicular to the plane of the drawing, the change in distance between the arms FE and DC is compensated for by the springs 29 and 35, so that the friction layer remains in contact with the disc 19 and the pin 17 remains in contact with the bottom of the groove 41.

Because the drive torque is determined by the product of the driving force of the drive pin and the distance between the pin and the centre of the disc, for given combinations of force variation and radius variation — or in other words, driving in the form of a traject — an unacceptably small drive torque could occur at a location in the groove which is not situated near the centre of the disc such as in the described case. The inclined portion of the groove will then be positioned at the relevant location.

What is claimed is:

1. A drive mechanism for the anti-scatter grid of an X-ray apparatus, comprising a driven parallelogram-like supporting arm construction which is pivotable in all directions about a pivot, an X-ray source being connected on one side of the pivot, on the other side of the pivot there being provided an image section comprising the said anti-scatter grid and a drive disc which is coupled to the anti-scatter grid and which is provided with a diametrically extending groove which cooperates with a drive pin, the said drive pin being connected to the supporting arm construction on the side of the pivot which is remote from the X-ray source and being slidable under spring pressure with respect to the supporting arm construction in a direction perpendicular to the plane of the disc, characterized in that the diametrical groove comprises an inclined portion which serves as a run-out for the drive pin and which has a maximum height which is substantially equal to the maximum depth of the diametrical groove, the drive pin being arranged in a resetting member which cooperates with the disc under friction and which bears on the one side against the disc under spring pressure and which on the other side is slidable in the lateral direction with respect to the disc under the force of two reset springs which are connected on the one end to the disc and on the other end to the resetting member.

2. A drive mechanism as claimed in claim 1, characterized in that the inclined portion is symmetrically situated with respect to the centre of the disc.

* * * * *